(12) United States Patent
Pohlscheidt et al.

(10) Patent No.: US 7,666,654 B2
(45) Date of Patent: Feb. 23, 2010

(54) METHOD FOR PREPARING VIRAL MATERIAL

(75) Inventors: Michael Pohlscheidt, Troisdorff (DE); Berthold Boedeker, Wuppertal (DE); Torsten Minuth, Berlin (DE); Heiner Apeler, Concord, CA (US); Uwe Langer, Wuppertal (DE); Katrin Brabender, Wuppertal (DE); Dirk Otto-Brabender, Wuppertal (DE); Joachim Kerper, Wuppertal (DE); Hans-Juergen Henzler, Solingen (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

(21) Appl. No.: 11/784,399

(22) Filed: Apr. 5, 2007

(65) Prior Publication Data

US 2008/0014626 A1 Jan. 17, 2008

Related U.S. Application Data

(63) Continuation of application No. PCT/EP2005/010810, filed on Oct. 7, 2005.

(30) Foreign Application Priority Data

Oct. 9, 2004 (DE) .................. 10 2004 049 290

(51) Int. Cl.
  *C12N 7/00* (2006.01)
  *C12N 7/02* (2006.01)
(52) U.S. Cl. .................. 435/235.1; 435/239
(58) Field of Classification Search .................. None
See application file for complete search history.

(56) References Cited

U.S. PATENT DOCUMENTS

| | | | |
|---|---|---|---|
| 5,719,051 | A | 2/1998 | Mundt et al. |
| 5,994,134 | A | 11/1999 | Giroux et al. |
| 6,194,210 | B1 | 2/2001 | Leu et al. |
| 6,455,298 | B1 | 9/2002 | Groner et al. |
| 6,656,720 | B2 | 12/2003 | Groner et al. |
| 6,726,907 | B1 | 4/2004 | Zhang et al. |
| 6,825,027 | B2 * | 11/2004 | Tauer et al. .................. 435/239 |

FOREIGN PATENT DOCUMENTS

| WO | WO 95/24468 | 9/1995 |
|---|---|---|
| WO | WO 98/33886 | 8/1998 |
| WO | WO -98/33886 | * 8/1998 |

(Continued)

OTHER PUBLICATIONS

GE Healthcare (2005) Microcarrier Cell Culture Principles and Methods. Handbook 18-1140-62.*

(Continued)

*Primary Examiner*—Mary E Mosher
*Assistant Examiner*—Stuart W Snyder
(74) *Attorney, Agent, or Firm*—Morrison & Foerster LLP

(57) ABSTRACT

The invention relates to a method for preparing viral suspensions. The invention relates in particular to a method for preparing high-titer viral suspensions in cell cultures. Preferred methods include increasing the volume of the cell culture prior to infection with viral material and subsequent further steps of expanding the volume to a final volume which is distinctly larger than the maximum culture volume prior to infection.

5 Claims, 1 Drawing Sheet

FOREIGN PATENT DOCUMENTS

| | | |
|---|---|---|
| WO | WO 99/57297 | 11/1999 |
| WO | WO 03/049767 | 6/2003 |

OTHER PUBLICATIONS

Widell, et al., A Microcarrier Cell Culture System for Large Scale Production of Hepatitis A Virus. J Virolog Meth. 1984; (8):63-71.*
Amersham, Manual Amersham Pharmacia (2001) Sweden (GE Healthcare, Microcarrier Cell Culture: Principles and Methods).
Baijot et al., Devel. Biol. Standard (1987) 66:523-530.
Chung et al., Biotechnology Progress (1993) 9(6):675-678.
Durrschmid et al., Biotechnoloy Prog. (2003) 19:1045-1048.
Durrschmid et al., Biotechnol. and Bioeng. (2003) 83(6):681-686.
Glacken et al., Annals New York Academy of Sciences (1983) 355-372.
Griffiths et al., Devel. Biol. Standard (1985) 66:331-338.
International Search Report for PCT/EP2005/010810, mailed on Dec. 23, 2005, 5 pages.
Lindner et al., Devel. Biol. Standard (1987) 66:299-305.
Merten et al., Cytotechnology (1994) 14:47-59.
Montagnon et al., Rev. of Infect. Diseases (1984) 6(2):S341-S344.
Montagnon et al., Devel. Biol. Standard (1984) 55:37-42.
Reiter et al., Cytotechnology (1990) 3:39-42.
Examination Report from Chinese Application No. 200580034446.5, issued Dec. 26, 2008.

* cited by examiner

METHOD FOR PREPARING VIRAL MATERIAL

CROSS-REFERENCE TO RELATED APPLICATIONS

This application is a continuation of copending International Patent Application PCT/EP2005/010810 filed on Oct. 7, 2005 and designating the United States, which was not published under PCT Article 21(2) in English, and claims priority of German Patent Application DE 10 2004 049 290.5 filed on Oct. 9, 2004. The contents of the above-referenced applications are incorporated herein by this reference in their entirety.

BACKGROUND OF THE INVENTION

1. Field of the Invention

The invention relates to a method for preparing viral suspensions. The invention relates in particular to a method for preparing high-titer viral suspensions in cell cultures. Preferred methods include increasing the volume of the cell culture prior to infection with viral material, and subsequent further steps of expanding the volume to a final volume which is distinctly larger than the maximum culture volume prior to infection.

2. Related Prior Art

The prior art has disclosed various methods for preparing viral material, in particular methods in which the viral material is prepared from animal cell cultures.

The skilled person distinguishes adherently growing cell lines, i.e. cell lines which preferably grow on solid surfaces, from cell lines which preferably grow in suspension. Adherently growing cell lines are either cultured directly on the surface of the culturing vessel used or they grow on solid particles (e.g. on microcarriers) which for their part may be suspended in a nutrient medium.

Methods for preparing viral material are known that use either cell lines growing in suspension or adherently growing cell lines.

Media composition is of great importance in the preparation of viral suspensions using cell cultures. In many cases, fetal calf serum (FCS) and growth factors of animal or plant origin must be added. Besides batch fluctuations and interfering protein components during downstream processing, the use of sera constitutes a biological safety risk (BSE/TSE, mycoplasma, prions etc.). Preference should therefore be given to serum-free, if possible synthetic, media [MERTEN ET AL. 1994].

The use of adherent cells, for example in microcarrier cultures, in particular causes, in addition to the typical technical barriers of scaling up, such as, for example, maintaining a sufficient oxygen supply, removing $CO_2$, adequate homogenization of the fermenter culture with minimum shearing stress, also and in particular problems with the inoculation of the next larger process scale [GLACKEN ET AL. 1983, J. B. GRIFFITHS ET AL. 1985, AMERSHAM 2001].

In this context, "direct migration" of purely adherently growing cells from carrier to carrier can take place only by manipulating the process in such a way that the cells lose at least partially their adherence due to said manipulation. Strategies for removing the adherence of adherently growing cells and enzymes which may be used for this are known to the skilled person [E. LINDNER ET AL. 1987, AMERSHAM 2001, DÜRRSCHMID ET AL. 2003] and must be taken into account in the development of said process with regard to removing or inactivating the enzymes used. In the 1970s and 1980s, successful experiments on direct cell migration from the container surfaces to microcarriers in roller bottles, Petri dishes and T flasks were carried out on smaller scales. A successful migration from carrier to carrier of adherently growing cells is known to the skilled worker only in fixed bed reactors, but this statement must be qualified by the fact that these are cell lines which grow both in suspension and adherently [AMERSHAM 2001, DÜRRSCHMID ET AL. 2003].

Particularly important is the way in which the process is carried out. The literature describes various methods such as, for example, batch or perfusion cultures. Perfusion cultures are used here for decoupling the dwell time from the specific growth rate, for avoiding inhibitions or limitations from the culture medium to increase productivity and are frequently run in "high density cell culture" (HDCC) mode over several months. However, in addition to complicated peripheral equipment (separator, spin filter, ultrasound cell retention, etc.), these systems require lengthy and complex start-up periods [M. REITER ET AL. 1990, GLACKEN ET AL. 1983, J. B. GRIFFITHS ET AL. 1985, AMERSHAM 2001, DÜRRSCHMID ET AL. 2003A].

It is also possible to supply enough nutrients by feeding the cell culture with highly concentrated substrate solutions. Inhibitions resulting from feeding, for example ammonium and/or lactate, may cause lower yields and productivities, in particular in HDCC mode. Up to now perfusion or dialysis systems have recommended themselves for avoiding inhibitory concentrations.

Process control problems may occur in the preparation of viral material by means of animal cell culture, which involves observing complex coupled kinetics of the cells and the virus, in particular when microcarrier cell cultures are used.

For example, the usefulness of propagating a CPE (cytopathic effect)-causing virus by complex perfusion is questionable, since said viruses usually destroy or lyse the cells within short periods of time (sometimes less than 3 to 7 days after infection).

The literature describes batch processes for virus propagation on the pilot and production scales (50 to 1000 l). Virus propagation is carried out with relatively low cell densities in all of the microcarrier processes described. After infection with the virus to be propagated, said infection continues up to the harvest, for example in the later final volume of the production scale [B. MONTAGNON ET AL. 1984, B. BAIJOT ET AL. 1987]. In some cases, perfusion cultures on the laboratory scale for slowly or non-lysing viruses have been described. In one case, a change of media to the original volume is described [AMERSHAM 2001].

U.S. Pat. No. 6,455,298 B1 and U.S. Pat. No. 6,656,720 B2 describe a method for preparing influenza virus material using cell lines growing in suspension. The disclosed method includes a first culturing phase in which the cell material is propagated in suspension culture, an infection step, and subsequently a second culturing phase in which the virus is produced. During this phase, the culture may be diluted further by adding medium or may be run like a perfusion culture. The advantage of this method is the fact that the capacity of said method is not limited by the limited size of the inner surface of the culturing vessels. Disadvantageously, however, a suspension culture cannot achieve cell densities as high as those possible by using microcarrier-based methods for virus production. Furthermore, the removal of cell material from the nutrient medium is considerably more complicated in suspension cultures than in microcarrier-based methods. These disadvantages are avoided in methods according to the present invention, since these make use of adherently growing cell lines on microcarriers for preparing viral material.

U.S. Pat. No. 6,726,907 and WO 95/24468 describe methods for preparing viral material, comprising a first culturing phase for propagating the cell material, an infection step and a subsequent second culturing phase in which the viral material is produced. In contrast to the methods of the invention, no further medium is added during the second culturing phase, and therefore the culture volume is not increased further during said second culturing phase. This results in a relatively small volume harvested, and the culture moreover also has a lower virus titer in comparison with the method of the invention.

U.S. Pat. Nos. 5,994,134, 5,719,051 and 6,194,210 disclose microcarrier-based methods for preparing viral material, which likewise include a first culturing phase, an infection step and a second culturing phase. In contrast to methods according to the present invention, this second culturing phase is not accompanied by any increase in the culture volume but is carried out as a perfusion culture. A continuous flow of fresh medium is supplied, while an equal volume flow of culture medium is removed, and the culture volume therefore remains constant. This method has an advantage over the method described above using suspended cell lines in that firstly a greater cell density can be achieved and secondly large amounts of virus-containing culture medium can be harvested over a longer period of time. However this microcarrier-based method for preparing viral material has a disadvantage in that the virus-containing culture media obtained have a lower virus titer (viral particles per unit volume) compared with the methods of the invention. This makes isolating the viral material more difficult and thereby increases the costs of the product. Furthermore, the supply of fresh medium and simultaneous removal of virus-containing culture broth make great demands on sterilization techniques and increase the risk of contaminations. It is not possible to use methods for preparing viral material with a second culturing phase in perfusion mode, if the virus to be produced causes the lysis of the producing cell and thereby a cytopathic effect (CPE).

This also applies to the complex method of external or internal dialysis, with mass transfer via semipermeable membranes having a specific molecular mass cut-off. To this end, the exhausted medium must be separated from the cells, before it is dialyzed with fresh medium via an externally applied membrane in a countercurrent or cocurrent process. Problems include, aside from the blocking of the membrane within the module by cell debris, etc., especially the complicated apparatus and scaling up.

SUMMARY OF THE INVENTION

In view of the above-described prior art, one technical problem underlying the present invention is that of providing a method for preparing viral material, which can produce large amounts of viral suspension containing a high concentration of said viral material in a relatively short time.

Said technical problem is solved according to the invention by a method for preparing viral material in a microcarrier cell culture, comprising (a) a first culturing phase which comprises an expansion of the cell culture volume by adding medium and microcarrier material, wherein a first maximum cell culture volume is obtained; (b) an infection step which is carried out after said first culturing phase and comprises the addition of infectious viral material to said microcarrier cell culture; (c) a second culturing phase which is carried out after said infection step and comprises a further expansion of the cell culture volume to a second maximum cell culture volume, with viral material being generated during said second culturing phase; and (d) a harvesting step for obtaining the viral material from the microcarrier cell culture, characterized in that said second maximum culture volume is distinctly larger than said first maximum culture volume. In a preferred embodiment of the invention, said second maximum culture volume is at least twice as large as said first maximum culture volume.

The invention relates to a method for preparing viral suspensions. Methods according to the invention have at least 2 culturing phases. During the first culturing phase (prior to the infection step), the culture volume is increased several times or continuously. In the method of the invention, the culture volume is further increased in steps or continuously even after the infection step, as a result of which the final volume to be harvested is distinctly larger than the maximum culture volume prior to infection.

The invention relates to:

A method for preparing viral material in a microcarrier cell culture, comprising (a) first culturing phase which comprises an expansion of the cell culture volume by adding medium and microcarrier material, wherein a first maximum cell culture volume is obtained; (b) an infection step which is carried out after said first culturing phase and comprises the addition of infectious viral material to said microcarrier cell culture; (c) a second culturing phase which is carried out after said infection step and comprises a further expansion of the cell culture volume to a second maximum cell culture volume, wherein the viral material being generated during said second culturing phase; and (d) a harvesting step for obtaining the viral material from the microcarrier cell culture, wherein said second maximum culture volume is larger than said first maximum culture volume.

It is preferred if said second maximum culture volume is from two to seven times larger than said first maximum culture volume.

It is furthermore preferred if said second maximum culture volume is from three to four times larger than said first maximum culture volume.

It is also preferred if said expansion of the cell culture volume is achieved by adding non-concentrated culture medium.

Moreover it is preferred if a serum-free medium is used.

In the method according to the invention it is preferred if a multiplicity of infection (MOI) of from 0.001 to 2 is applied in the infection step.

Another object of the invention is a viral material prepared by before-mentioned method according to the invention.

Another object of the invention is a purified viral material prepared by the method according to the invention.

A further object of the invention is a purified and formulated viral material prepared by the method according to the invention.

The core of the invention is a significant sequential or continuous increase in the production volume, preferably with medium of the same kind or with medium of a similar kind. The increase in efficiency compared with classical methods is described below for the example of propagation of Parapoxvirus ovis.

An advantage of the methods of the invention is in particular the fact that the virus titer of the culture broth can be increased tenfold over the batch process by feeding in medium after the infection step. A particular advantage is the fact that said increase in the virus titer can also be achieved if non-concentrated medium is fed in after the infection step, thereby again substantially increasing the culture volume during the second culturing phase. The total amount of viral material produced can therefore again be increased considerably over the method of the invention in which concentrate is fed.

Further embodiments of the invention are revealed to the skilled person by studying the examples and illustrations listed hereinbelow.

DESCRIPTION OF PREFERRED EMBODIMENTS

Example 1

Figure 1:
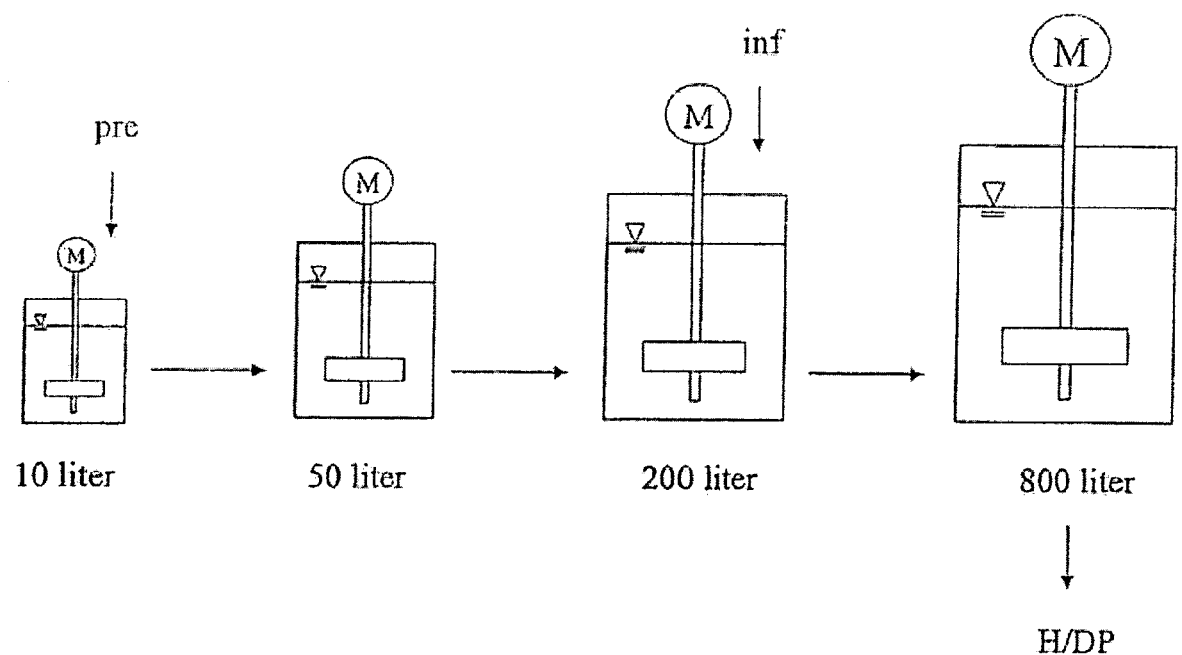
FIG. 1: Exemplary representation of the method of the invention with volume changes from 10 liter via 50 liter and 200 liter to 800 liter. The infection is carried out on the 200-liter scale (abbreviations: pre, preculture; inf, infection; H/DP, harvest/downstream processing).

First, a known adherent bovine kidney cell line was cultured in stationary cultures (tray stacks, roller bottles) or in a batch microcarrier cell culture. For this purpose, a microcarrier concentration of from 1 to 8 g/l, preferably 3 to 7 g/l, was used. The reactor was inoculated with from 1 to $6*10^5$ cells/ml. After the nutrients had been consumed, a change of media by way of sedimentation of the microcarriers was carried out during this cell propagation phase. After the maximum cell number, from 0.2 to $2*10^7$ cells/ml, preferably 0.3 to $0.7*10^7$ cells/ml, have been reached, the culturing using supplement-containing media comprised carrying out washing steps by way of multiple sedimentation and replacement of the supernatant with medium without supplements or distinctly lower supplement concentration, in order to reduce the concentration of the supplements such as, for example, FCS, growth hormones, etc. This was followed by infection with a multiplicity of infection (MOI) of from 0.001 to 2, preferably from 0.005 to 0.1.

Said infection was carried out in a culture volume of from 10 to 100% of the fermenter volume. The infection continued without further manipulation in the batch mode for about 3 to 15 days, preferably 7 to 11 days. Upon achieving a cytopathic effect (CPE) of the infected cells of from 40 to 100%, preferably 40-90%, the culture was harvested.

Gas is supplied, for example, by way of bubble-free and low-shearing membrane gassing. The $pO_2$ is regulated to from 15 to 65%, preferably from 25 to 55%.

The pH is regulated with sodium hydrogen carbonate, sodium hydroxide and/or $CO_2$ gas to from pH 6.6 to pH 7.6, preferably pH 6.9 to pH 7.5. The temperature is from 32° C. to 37° C. The regulated parameters may be different in the cell growth phase and the virus propagation phase.

Further optimization of the virus yield may be achieved by feeding medium concentrates or concentrates of individual substrates during the virus propagation phase. This kind of process control has been established and described for various systems. However, in particular when using adherent cell lines for virus propagation in microcarrier cultures, determination of essentially required specific rates of consumption is extremely difficult, correlating to some extent with the problems with determining the cell number, known to the expert. Even if individual rates of consumption of substrates are known, there is the additional question of inhibitions of the culture. The literature describes especially limitations due to ammonium or lactate. There is no generally valid threshold which must therefore be determined specifically for the biological system used.

If a limitation/inhibition has been detected, it must be avoided in order to achieve high product titers. In recent years therefore, use has been made, in particular in the field of HDCC, of perfusion or dialysis cultures whose disadvantages with regard to propagation of a CPE-causing virus have been discussed above.

Example 2

The following is a comparison of the volume-expanded fed batch (VEF) method according to the invention with methods disclosed in the prior art.

The abovementioned sequential volume expansion by way of diluting the culture with fresh medium after infection (for example to get to the process one scale up: 1:2-1:7, preferably 1:3-1:5) astonishingly did not show the expected virus titer reduction, but surprisingly an average 8 to 13 fold increase in the titer despite dilution. This was achieved, although the volume was increased significantly by a factor of from 2 to 7, preferably a factor of from 3 to 4, in comparison with the described batch process. This results in a dramatically improved virus yield.

Using the comparative methods described, such as, for example, dialysis, concentrate feeds, perfusion and/or simple reduction in the cell number, all of which were carried out several times, it was not possible to achieve or increase said yields (Table 1).

Comparison of known methods with the volume-expanded fed batch method, beginning by way of example in the 3.5 liter reactor. Runs with comparable run time and comparable cell number for PPVO propagation by means of an adherent BK cell line are depicted by way of example. The culturing conditions were mentioned above in the description of the batch process and also apply to the other methods. For dialysis, a module with a 20 kD molecular mass cut-off was used, with the preculture being carried out in perfusion mode. Said dialysis was carried out in a countercurrent process. Relative values based on the batch culture are shown.

TABLE 1

|  | Batch | Dialysis | Fed Batch [with concentrated medium] | VEF Batch [with non-concentrated medium] |
| --- | --- | --- | --- | --- |
| $TCID_{50}$ [based on batch] | 1 | 10 | 9 | 10 |
| Final volume [based on batch] | 1 | 1 | 1 | 4 |
| Productivity [based on batch] | 1 | 10 | 9 | 40 |

Positive results in addition to the distinctly increased virus yields can be recognized especially also in downstream processing. These are especially evident in the form of lower cell contaminations such as host cell proteins, proteins and DNA per unit dose (particularly important when applying vaccine-like human therapeutics), and smaller losses of yield after filtration. A 20 μm filtration, for example, achieves on average a loss of ~0.6 l log $TCID_{50}$ in batch mode. In comparison, the loss is only 0.1-0.4 log $TCID_{50}$ in the VEF batch.

Volume expansion likewise favorably affects the above-described technical barriers of scaling up. In the case of oxygen supply, for example by way of the low-shearing and foaming-avoiding method of membrane gassing, successive volume expansion by dilution can achieve a significant increase in scale (resulting from physical parameters of the reactors), since less oxygen has to be introduced to the system due to reduction in the cell number as a result of dilution and lysis by the virus. To afford better understanding, FIG. 1 depicts by way of example the method on a production-relevant scale. The steps illustrated, in particular with respect to frequency and efficiency of direct migration when transferring the BK cell to the next fermentation scale, were confirmed experimentally. No effects on productivity were found.

The example starts with inoculation of the 10 liter reactor. The process is controlled as described above for the batch mode. Upon reaching confluence, a direct 1:5 dilution to the 50 liter scale is carried out with fresh microcarriers in the same or a comparable ratio to the medium as on the 10 liter scale. Upon reaching confluence again, the same method is used to inoculate the 200 liter reactor. A brief sedimentation with or without internal stirring may be advantageous.

If serum-containing/proteinaceous medium has been used during the growth phase, washing steps with serum- and protein-free medium are carried out to reduce supplement concentration. The infection is carried out as in the batch process, with the MOI described.

The VEF batch is then started 10-36 hours after infection. This involves a secure and robust dilution of the suspension with fresh culture medium, and this may be carried out in the same reactor or in larger reactors. This requires only little effort. The 200 liter virus-cell suspension is increased, for example, to 400 liter, then to 600 liter, and finally to 800 liter, stepwise in adequate time intervals and/or continuously. Surprisingly, this did not result in a deterioration of virus productivity, as described above and illustrated in table 1.

Differences between cells cultured in serum-containing, proteinaceous and synthetic medium were not found here. No differences with respect to migration from carrier to carrier, cell number and productivity were found for the example of bovine kidney cell lines adapted to serum-free and synthetic conditions. This means that the method can be used for serum-containing, proteinaceous and synthetic culture media.

TABLE 2

Exemplary comparison of the $TCID_{50}$ of the BK cell line adapted to serum-containing, serum-free and synthetic conditions for propagation of the PPVO virus by various methods, based on a normalized titer (here serum-containing)

|  | Serum-containing | Proteinaceous | Synthetic |
|---|---|---|---|
| Roller bottle | 1 | 0.9 | 1 |
| Batch culture | 1 | 1.1 | 1 |
| VEF batch | 1 | 0.9 | 1.1 |

The advantages according to the invention of the volume-expanded fed batch described over the established and known methods may be summarized as follows: (1) it is a safe, robust and efficient method for virus propagation. (2) Higher virus yields are achieved. (3) There is no increased requirement for complicated apparatus. (3) Process control is comparatively simple. (4) The number of persons needed for supervising the process is low. (5) Product quality is improved, particularly with regard to downstream processing. (6) Larger fermenters may be used. (7) The method is readily scalable. (8) The method is adaptable to various serum-containing, serum-free, proteinaceous and synthetic culture media.

Example 3

Propagation of PPVO in a 10 liter stirred tank by means of microcarrier cell culture in batch mode using a proteinaceous medium.

The bovine kidney cell line adapted to serum-free but proteinaceous conditions was cultured, starting from the cell bank, first in T flasks and then in roller bottles. Culturing was carried out at 37° C. and a pH of 7.2+/−0.2 in a $CO_2$ incubator. The cell material was harvested by trypsinization.

The concentration of the Cytodex 3 microcarriers, Amersham, Sweden, which were prepared according to the supplier's instructions, was 3 g/l. Inoculation was carried out in a 10 liter volume with a cell number of 2 E05 cells/ml. During the cell culturing phase media were changed by means of sedimentation at a glucose concentration of $c<0.5$ g/l. The reactor was stirred at 30 rpm with the aid of an anchor stirrer. The $pO_2$ was regulated to 40%+/−10%. The pH was 7.2+/−0.2.

After 10 days, a cell number of 3.1 E06 cells/ml was reached, with the cells being in the stationary growth phase. After three washing steps with medium without supplements, the final volume was infected with PPVO (MOI=0.01).

No manipulations were carried out during the subsequent virus propagation. After 8 days, a CPE of 90% was achieved. The fermentation was stopped upon sedimentation by 20 μm filtration. Table 3 depicts the $TCID_{50}$ at the time of harvest and after harvest.

TABLE 3

$TCID_{50}$ in batch fermentation described by way of example

| | Before harvest | After harvest | Volume |
|---|---|---|---|
| $\log_{10}(TCID_{50})$ [$\log_{10}$ (l/ml)] | 6.7 +/− 0.3 | 6.0 +/− 0.3 | ~10 l |

Example 4

Propagation of PPVO in a 3.5 liter stirred tank by means of microcarrier cell culture in volume-expanded fed batch (transfer to 15 liter reactor) using a proteinaceous medium.

The bovine kidney cell line adapted to serum-free but proteinaceous conditions was cultured, starting from the cell bank, first in T flasks and then in roller bottles. Culturing was carried out at 37° C. and a pH of 7.2+/−0.2 in a $CO_2$ incubator. The cell material was harvested by trypsinization.

The concentration of the Cytodex 3 microcarriers, Amersham, Sweden, which were prepared according to the supplier's instructions, was 5 g/l. Inoculation was carried out in a 3.5 liter volume with a cell number of 3×10E5 cells/ml. During the cell culturing phase media were changed by means of sedimentation at a glucose concentration of $c<0.5$ g/l. The reactor was stirred at 45 rpm with the aid of an anchor stirrer. The $pO_2$ was regulated to 40%+/−10%. The pH was 7.2+/−0.2.

After 10 days, a cell number of 7.1×10^6 cells/ml was reached, with the cells being in the stationary growth phase. After three washing steps with medium without supplements, a 1.7 liter volume was infected with PPVO (MOI=0.01) at n=14 rpm for 2 h, and then increased to 3.5 liter, and the stirrer revolutions were increased to n=45 rpm.

16 h after infection, the entire culture was transferred to the 15 liter reactor and 7 liters were added (1:2 dilution). The same parameters were regulated in the 15 liter reactor.

46 h after infection, the culture was diluted to 10.5 liter (1:3 dilution based on 3.5 l). The CPE was approximately 30%, based on the cell number in the 3.5 liter reactor and taking into account the dilution.

70 h after infection, the volume was increased to 12.5 liter and finally, 94 h after infection, to 13.8 liter (1:3.9 dilution).

Seven days after infection (2.5 days after the last dilution), the fermentation was stopped by sedimentation and subsequent 20 μm filtration of the culture (CPE=93%).

Table 4 depicts the $TCID_{50}$ at the time of harvest and in the harvest.

TABLE 4

$TCID_{50}$ in the VEF batch of the invention

|  | Before harvest | After harvest | Volume |
|---|---|---|---|
| $\log_{10}(TCID_{50})$ [$\log_{10}$ (l/ml)] | 7.7 +/− 0.3 | 7.6 +/− 0.3 | 14 liter |

Example 5

Propagation of PPVO in a 3.5 liter stirred tank by means of microcarrier cell culture in volume-expanded fed batch (transfer to 15 liter reactor) using a protein-free and serum-free medium.

The bovine kidney cell line adapted to synthetic conditions was cultured, starting from the cell bank, first in T flasks and then in roller bottles. Culturing was carried out at 37° C. and a pH of 7.2+/−0.2 in a $CO_2$ incubator. The cell material was harvested by trypsinization.

The concentration of the Cytodex 3 microcarriers, Amersham, Sweden, which were prepared according to the supplier's instructions, was 5 g/l. Inoculation was carried out in a 3.5 liter volume with a cell number of $3.8 \times 10^5$ cells/ml. During the cell culturing phase media were changed by means of sedimentation at a glucose concentration of c<0.5 g/l. The reactor was stirred at 45 rpm with the aid of an anchor stirrer. The pO2 was regulated to 40%+/−10%. The pH was 7.2+/−0.2.

After 13 days, a cell number of 5.6 E06 cells/ml was reached, with the cells being in the stationary growth phase. After three washing steps with the same medium, a 3.5 liter volume was infected with PPVO (MOI=0.01), n=40 rpm.

20 h after infection, the entire culture was transferred to the 15 liter reactor and 7 liters were added (1:2 dilution). The same parameters were regulated in the 15 liter reactor.

49 h after infection, the culture was diluted to 11 liter (1:3 dilution based on 3.5 l). The CPE was approximately 30%, based on the cell number in the 3.5 liter reactor and taking into account the dilution.

69 h after infection, the volume was increased to 12.5 liter and finally, 86 h after infection, to 13.5 liter (1:3.9 dilution).

Seven days after infection, the fermentation was stopped by sedimentation and subsequent 20 μm filtration of the culture (CPE=93%).

Table 5 depicts the $TCID_{50}$ at the time of harvest and after harvest.

TABLE 5

Representation of the $TCID_{50}$ achieved in VEF batch fermentation using the synthetic cell line, as described in the example.

|  | Before harvest | After harvest | Volume |
|---|---|---|---|
| $\log_{10}(TCID_{50})$ $TCID_{50}$ [l/ml] | 7.8 +/− 0.3 | 7.4 +/− 0.3 | ~14 l |

Example 6

In order to obtain highly purified viral preparations, microcarrier-free virus harvests were used. The virus propagation was carried out, for example, as described in examples 1 to 5. First, a gentle microfiltration was carried out with the virus harvest. For this purpose, for example, a cartridge holder from Sartorius (Germany) with a membrane cartridge from Sartorius (Germany) can be employed. Alternatively it is also possible to use hollow fiber modules from Minntech (USA) or Pall (USA). Preference is given to using for microfiltration membranes or hollow fibers with a pore size of 0.1 μm. The microfiltration stage is used to reduce the volume 5 to 20 fold, to condition the pH (preferably pH 7.5 to 9.0) and to dilute low molecular weight coingredients of the fermentation. The viral concentrate obtained in this way was chemically inactivated with ethyleneimine at pH 8.6, using an ethyleneimine concentration of from 3 to 20 mM for virus inactivation. Said inactivation was carried out in two stages. The reaction mixture was first incubated with pH control at 37° C. for 3 to 6 h, and virus inactivation was then finished in a further reaction vessel at 37° C. overnight. The inactivated virus suspension was neutralized by adding a 1.5 to 3.0 molar excess of sodium thiosulfate. Neutralization was followed by low-revolution centrifugation at 4000 to 8000 g for 2 to 4 h. This first purification step served to remove the viral particles from the neutralized inactivation solution. After this first purification stage, the inactivated viral particles may be stored at 2 8° C. or at <−65° C. until further processing. The second purification stage may be carried out, for example, by way of low-revolution centrifugation using a 20% saccharose cushion. Alternatively, however, it is also possible to use membrane adsorbers from Sartorius (Germany) or Pall (USA). The second centrifugation stage was carried out at 4000 to 8000 g overnight. The purification process is analyzed by means of asymmetric flow-field-flow fractionation (AF4 analysis) and refractometry and also quantifying electron microscopy. Tables 6 or 7 depict typical yield profiles.

TABLE 6

Analysis of the above-described purification process by means of asymmetric flow-field-flow fractionation (AF4 analysis) and refractometry

| Experiment No. | Process stage | Sample | Total particles | Cumulative yield [%] |
|---|---|---|---|---|
| 508623 | 3.0/0.8 μm Particle filtration | Start | 5.9E13 | 100 |
|  |  | Filtrate | 2.5E13 | 42 |
|  | Centrifugation stage 1 | Start | 2.5E13 |  |
|  |  | Sediment | 5.5E12 | 9 |
|  | Centrifugation stage 2 | Start | 5.5E12 |  |
|  |  | Sediment | 3.6E12 | 6 |

TABLE 6-continued

Analysis of the above-described purification process by means of asymmetric flow-field-flow fractionation (AF4 analysis) and refractometry

| Experiment No. | Process stage | Sample | Total particles | Cumulative yield [%] |
|---|---|---|---|---|
| 508624 | 3.0/0.8 μm | Start | 6.6E13 | 100 |
| | Particle filtration | Filtrate | 2.3E13 | 35 |
| | Centrifugation stage 1 | Feed | 2.3E13 | |
| | | Sediment | 5.9E12 | 9 |
| | Centrifugation stage 2 | Feed | 5.9E12 | |
| | | Sediment | 3.6E12 | 5 |
| 508627 | 3.0/0.8 μm | Start | 3.6E13 | 100 |
| | Particle filtration | Filtrate | 1.5E13 | 43 |
| | Centrifugation stage 1 | Feed | 1.5E13 | |
| | | Sediment | 3.1E12 | 8 |
| | Centrifugation stage 2 | Feed | 3.1E12 | |
| | | Sediment | 2.0E12 | 5 |
| | | Average yield | | 5 |

TABLE 7

Analysis of the above-described purification process by means of quantifying electron microscopy

| Experiment No. | Process stage | Sample | Total particles | Cumulative yield [%] |
|---|---|---|---|---|
| 508623 | 3.0/0.8 μm | Start | 1.5E13 | 100 |
| | Particle filtration | Filtrate | n.d. | — |
| | Centrifugation stage 1 | Feed | n.d. | — |
| | | Sediment | 4.4E12 | 30 |
| | Centrifugation stage 2 | Feed | 4.5E12 | — |
| | | Sediment | 4.2E12 | 29 |
| 508624 | 3.0/0.8 μm | Start | 2.4E13 | 100 |
| | Particle filtration | Filtrate | n.d. | — |
| | Centrifugation stage 1 | Feed | n.d. | — |
| | | Sediment | 4.6E12 | 19 |
| | Centrifugation stage 2 | Feed | 4.6E12 | — |
| | | Sediment | 3.2E12 | 13 |
| 508627 | 3.0/0.8 μm | Start | 7.3E12 | 100 |
| | Particle filtration | Filtrate | n.d. | — |
| | Centrifugation stage 1 | Feed | n.d. | — |
| | | Sediment | 2.3E12 | 31 |
| | Centrifugation stage 2 | Feed | 2.3E12 | — |
| | | Sediment | 3.5E12 | 48 |
| | | Average yield | | 13-48 |

The host cell protein content at selected process stages was determined using a specific host cell protein assay and used for determining dilution factors. Typical dilution results are depicted in Table 8.

TABLE 8

Dilution of host cell proteins during virus purification

| Experiment No. | Process stage | Sample | HCP content [μg/1E10 VPs] | Cumulative HCP dilution |
|---|---|---|---|---|
| 508623 | 3.0/0.8 μm | Pre-filtration | 58 | — |
| | Particle filtration | Post-filtration | n.d. | — |
| | Centrifugation stage 1 | Feed | n.d. | — |
| | | Sediment | 3.5 | 17 |
| | Centrifugation stage 2 | Feed | 3.5 | — |
| | | Sediment | 3 | 19 |

TABLE 8-continued

Dilution of host cell proteins during virus purification

| Experiment No. | Process stage | Sample | HCP content [μg/1E10 VPs] | Cumulative HCP dilution |
|---|---|---|---|---|
| 508624 | 3.0/0.8 μm | Pre-filtration | 80 | — |
| | Particle filtration | Post-filtration | n.d. | — |
| | Centrifugation stage 1 | Feed | n.d. | — |
| | | Sediment | 4.8 | 17 |
| | Centrifugation stage 2 | Feed | 4.8 | — |
| | | Sediment | 5 | 16 |
| 508627 | 3.0/0.8 μm | Pre-filtration | 187 | — |
| | Particle filtration | Post-filtration | n.d. | — |
| | Centrifugation stage 1 | Feed | n.d. | — |
| | | Sediment | 14 | 13 |
| | Centrifugation stage 2 | Feed | 14 | — |
| | | Sediment | 14 | 13 |
| | | Average dilution | | 13-19 |

Microbial purity was checked using the customary standard methods. It was shown that the above-described purification process can be carried out under aseptic conditions.

TABLE 9

Evaluation of microbial purity

| Experiment No. | Process stage | Sample | Bioburden [counts/ml] |
|---|---|---|---|
| 508623 | 3.0/0.8 μm | Start | 0/0 |
| | Particle filtration | Filtrate | 0/0 |
| | Centrifugation stage 1 | Feed | — |
| | | Sediment | 0/0 |
| | Centrifugation stage 2 | Feed | — |
| | | Sediment | 0/0 |
| 508624 (02KUR02) | 3.0/0.8 μm | Start | 0/0 |
| | Particle filtration | Filtrate | 0/0 |
| | Centrifugation stage 1 | Feed | — |
| | | Sediment | 0/0 |
| | Centrifugation stage 2 | Feed | — |
| | | Sediment | 0/0 |
| 508627 (02KUR05) | 3.0/0.8 μm | Start | 0/0 |
| | Particle filtration | Filtrate | 0/0 |
| | Centrifugation stage 1 | Feed | — |
| | | Sediment | 1/0 |
| | Centrifugation stage 2 | Feed | — |
| | | Sediment | 0/0 |

Following the second purification stage, the highly pure viral preparation was formulated using microfiltration. Membranes from Sartorius (Germany) or Pall (USA) and hollow fibers from Minntech (USA) or Amersham Biosciences (USA) may be employed for this formulation stage. The preferred port size is 0.1 μm. The purpose of this formulation stage consists of conditioning the virus suspension with respect to pH, osmolality and particle content. After addition of a suitable stabilizer (1-5% polygeline), the viral preparation produced in this way may be lyophilized for long-term storage. Prior to its use as medicament, the lyophilisate must be admixed with sterile, pyrogen-free WFI (water for injection), according to the starting volume. The viral composition prepared by means of the above-described procedure is suitable for parenteral applications.

Table 10 summarizes typical results of the characterization of the formulated viral preparation prior to freeze drying.

TABLE 10

Analysis of the formulated virus suspension prior to freeze drying

| Parameter | 508623 | 508624 | 508627 |
|---|---|---|---|
| Particle content AF4/RI [VPs/ml] | 1.8E10 | 2.0E10 | 1.0E10 |
| Particle content by means of quantifying electron microscopy [VPs/ml] | 4.15E10 | 3.58E10 | 2.5E10 |
| Biological activity (transgenic HBV mouse) | | corresponds to | |
| Bioburden [counts/ml] | 0 | 0 | 0 |
| Endotoxin content [EU/ml]* | 6 | 6 | 2.4 |
| Host cell protein content [µg/ml] | 4.7-6.4 | 8.6-9.3 | 9.9-13.3 |
| Nucleic acid content [ng/ml] | 3.7 | 2.9 | 1.6 |

*the virus stabilizer used already has an average endotoxin content of from 2 to 8 EU/ml.

Patents

U.S. Pat. No. 6,455,298
U.S. Pat. No. 6,656,720
U.S. Pat. No. 5,994,134
U.S. Pat. No. 5,719,051
U.S. Pat. No. 6,194,210
U.S. Pat. No. 6,726,907
WO 95/24468

REFERENCES

AMERSHAM, "Microcarrier Cell Culture-Principals and Methods", Manual Amersham Pharmacia, Sweden (2001)

B. BAIJOT, M. DUCHENE, J. STEPHENNE, "Production of Aujesky Vaccine by the Microcarrier Technology", Devel. Biol. Standard (1987) 66:523-530

M. P. DÜRRSCHMID, K. LANDAUER, G. SIMIC, H. KLUG, T. KEIJZER, F. TRAMPLER, A. OUDSHOORN, M. GRÖSCHL, D. MÜLLER, O. DOLBHOFF-DIER, "Comparison of Fluidized Bed and Ultrasonic Cell Retention Systems for High Cell Density Mammalian Cell Culture", Biotechnol. Prog. (2003) 19:1045-1048

M. P. DÜRRSCHMID, K. LANDAUER, G. SIMIC, G. BLÜML, O. DOLBHOFF.DIER, "Scaleable Inoculation Strategies for Microcarrier Based Animal Cell Bioprocesses", Biotechnol. And Bioeng. (2003) 83, No. 6

M. W. GLACKEN, R. J. FLEISCHAKER, A. J. SINSKEY, "Large Scale Production of Mammalian Cells and Their Products", in Annals New York Academy of Sciences (1983) 355-372

J. B. GRIFFITHS, D. R. CAMERON, D. LOBBY, "A Comparison of Unit Process Systems for Anchorage Dependent Cells", Devel. Biol. Standard (1985) 66:331-338

E. LINDNER, A.-C. ARVIDSSON, I. WERGELAND, D. BILLIG, "Subpassaging Cells on Microcarriers", Devel. Biol. Standard (1987) 66:299-305

MERTEN, O. W., KIERULFF J. V., CASTINGOLLES, N., PERRIN, P, "Evaluation of the new serum free medium (MSDSS2) for the production of different biologicals: Use of various cell lines", Cytotechnol. (1994) 14:47-59

B. J. MONTAGNON, B. FANGET, J. C: VINCENT-FALQUET, "Industrial Scale Production of Inactivated Poliovirus Vaccine Prepared by Culture of Vero Cells on Microcarrier", Rev. Of Inf. Diseases (1984) 6, Supplement 2

B. J. MONTAGNON, J. C: VINCENT-FALQUET, B. FANGET, "Thousand Liter Scale Microcarrier Culture of Vero Cells for Killed Polio Viruses Vaccine", Devel. Biol. Standard (1984) 55:37-42

M. REITER, F. WEIGANG, W. ERNST, "High Density Microcarrier Culture with a New Device which Allows Oxygenation and Perfusion of Microcarrier Cultures", Cytotechnology (1990) 3:39-42

The invention claimed is:

1. A method for preparing viral material in a microcarrier cell culture, comprising
    (a) a first culturing phase which comprises an expansion of the cell culture volume by adding medium and microcarrier material, wherein a first maximum cell culture volume is obtained;
    (b) an infection step which is carried out after said first culturing phase and comprises the addition of infectious viral material to said microcarrier cell culture;
    (c) a second culturing phase which is carried out after said infection step and comprises a further expansion of the cell culture volume to a second maximum cell culture volume, wherein the viral material being generated during said second culturing phase; and
    (d) a harvesting step for obtaining the viral material from the microcarrier cell culture,
  wherein said second maximum culture volume is larger than said first maximum culture volume,
  wherein prior to the infection step (b) the cell culture volume is increased continuously, and
  wherein said second maximum culture volume is from two to seven times larger than said first maximum culture volume.

2. The method of claim 1, wherein said second maximum culture volume is from three to four times larger than said first maximum culture volume.

3. The method of claim 1, in which said expansion of the cell culture volume is achieved by adding non-concentrated culture medium.

4. The method of claim 1, in which a serum-free medium is used.

5. The method of claim 1, in which a multiplicity of infection (MOI) of from 0.001 to 2 is applied in the infection step.

* * * * *